(12) United States Patent
Thal (10) Patent No.: US 6,638,283 B2
(45) Date of Patent: Oct. 28, 2003

(54) SURGICAL SUTURE PASSER

(76) Inventor: Raymond Thal, 11321 Bright Pond La., Reston, VA (US) 22094

( * ) Notice: Subject to any disclaimer, the term of this patent is extended or adjusted under 35 U.S.C. 154(b) by 0 days.

(21) Appl. No.: 10/053,624

(22) Filed: Jan. 24, 2002

(65) Prior Publication Data

US 2002/0103493 A1 Aug. 1, 2002

Related U.S. Application Data

(60) Provisional application No. 60/264,374, filed on Jan. 26, 2001.

(51) Int. Cl.[7] .............................................. A61B 17/04
(52) U.S. Cl. ......................... 606/144; 606/148; 606/223
(58) Field of Search .............................. 606/144, 148, 606/223

(56) References Cited

U.S. PATENT DOCUMENTS

| | | | |
|---|---|---|---|
| 4,527,564 A | * 7/1985 | Eguchi et al. .............. | 606/223 |
| 4,923,461 A | 5/1990 | Caspari et al. ............. | 606/146 |
| 4,935,027 A | 6/1990 | Yoon ........................... | 606/146 |
| 5,250,055 A | 10/1993 | Moore et al. ............... | 606/148 |
| 5,320,633 A | 6/1994 | Allen et al. ................. | 606/144 |
| 5,467,786 A | 11/1995 | Allen et al. ................. | 128/898 |
| 5,470,337 A | 11/1995 | Moss ........................... | 606/139 |
| 5,522,820 A | 6/1996 | Caspari et al. ............. | 606/148 |
| 5,776,150 A | 7/1998 | Nolan et al. ................ | 606/148 |
| 5,792,177 A | 8/1998 | Kaseda ....................... | 606/205 |
| 5,824,009 A | 10/1998 | Fukuda et al. ............. | 606/139 |
| 5,846,254 A | 12/1998 | Schulze et al. | |
| 5,871,490 A | 2/1999 | Schulze et al. | |
| 5,895,395 A | 4/1999 | Yeung | |
| 5,899,921 A | 5/1999 | Caspari et al. | |
| 5,902,321 A | 5/1999 | Caspari et al. | |
| 5,935,149 A | 8/1999 | Ek | |
| 5,961,530 A | 10/1999 | Moore et al. | |
| 6,051,006 A | 4/2000 | Shluzas et al. | |
| 6,086,601 A | 7/2000 | Yoon | |

* cited by examiner

*Primary Examiner*—Gary Jackson
(74) *Attorney, Agent, or Firm*—Hoffman, Wasson & Gitler, P.C.

(57) ABSTRACT

The suture passer of the invention has a pair of opposed jaws. The lower jaw is formed by a hollow tube having its end turned upwardly to face the upper jaw. The hollow tube preferably extends from the lower jaw to a pair of handles. The tube can terminate anywhere along the length of the lower jaw. An upper jaw is hinged to the tube and provides a guide for a needle. The handles are used for the surgeon to grasp the device and to manipulate the jaws.

17 Claims, 12 Drawing Sheets

SURGICAL SUTURE PASSER

The instant application is based upon provisional application Ser. No. 60/264,374, filed Jan. 26, 2001.

BACKGROUND OF THE INVENTION

Many surgical procedures entail the use of sutures to repair tissue. A suture is passed through the tissue and secured. The tissue to be repaired often needs to be manipulated or grasped in order to properly position the sutures.

The surgeon repairing the tissue needs to attach sutures both quickly and accurately. The sutures need to be attached to tissue with causing a minimum amount of fatigue to the surgeon. There are prior art devices used to facilitate the process of attaching sutures to tissue.

U.S. Pat. No. 4,923,461 (Caspari et al) discloses a method for suturing tissue. A suture passer having a pair of opposed jaws is used by a surgeon. A suture passes through a tube until it reaches the lower jaw. A needle in the lower jaw of the instrument passes through an aperture in the upper jaw. The jaws are manipulated to grasp the tissue to be sutured.

Another prior art device is disclosed by Fukuda et al (U.S. Pat. No. 5,824,009). Fukuda et al discloses a suture guide having a pair of opposed jaws. The upper jaw has a forked end formed by a slot and aperture. The suture attached to a needle passes through the top jaw and is deflected into a container in the lower jaw for containing the needle with the suture.

U.S. Pat. No. 5,895,395 (Yeung) discloses a suture device having a suture delivery needle and a suture receiving needle. A shaped memory needle initially is held by the delivery needle but is manipulated to extend into the receiving needle.

There is a need for a suture delivery device that manipulates the tissue to be sutured and allows for accurate suture passage.

It is an object of the invention to provide a arthroscopic or open suture passer that has a pair of opposed jaws for manipulating the tissue to be sutured and providing a guide for a needle attached to the suture.

It is another object of the invention to provide an arthroscopic or open suture passer that allows a surgeon to quickly and accurately pass a suture through tissue.

It is yet another object of the invention to provide a suture passer that reduces fatigue for the surgeon performing an operation involving sutures.

It is another object of the invention to provide a suture passer which is easy for a surgeon to use and operate.

These and other objects of the invention will become apparent to one of ordinary skill in the art after reviewing the disclosure of the invention.

SUMMARY OF THE INVENTION

The suture passer of the invention has a pair of opposed jaws. The lower jaw is formed by a hollow tube having its end turned upwardly to face the upper jaw. The hollow tube preferably extends from the lower jaw to a pair of handles. The tube can terminate anywhere along the length of the lower jaw. An upper jaw is hinged to the tube and provides a guide for a needle. The handles are used for the surgeon to grasp the device and to manipulate the jaws.

The handles are used to manipulate the jaws to grasp the tissue between them. Once tissue is grasped, a needle is passed through the guide of the upper jaw and tissue and into the open end of the lower jaw tube. The needle is deflected within the lower jaw and extends through the tube. The needle is long and flexible enough to be deflected out of the grasper or retained in the tube. In place of a tube, the lower jaw may have a slot retaining the needle. If retained in the tube or by the jaw, the suture passer is removed and the surgeon then accesses the needle.

DETAILED DESCRIPTION OF THE INVENTION

Figure 1:
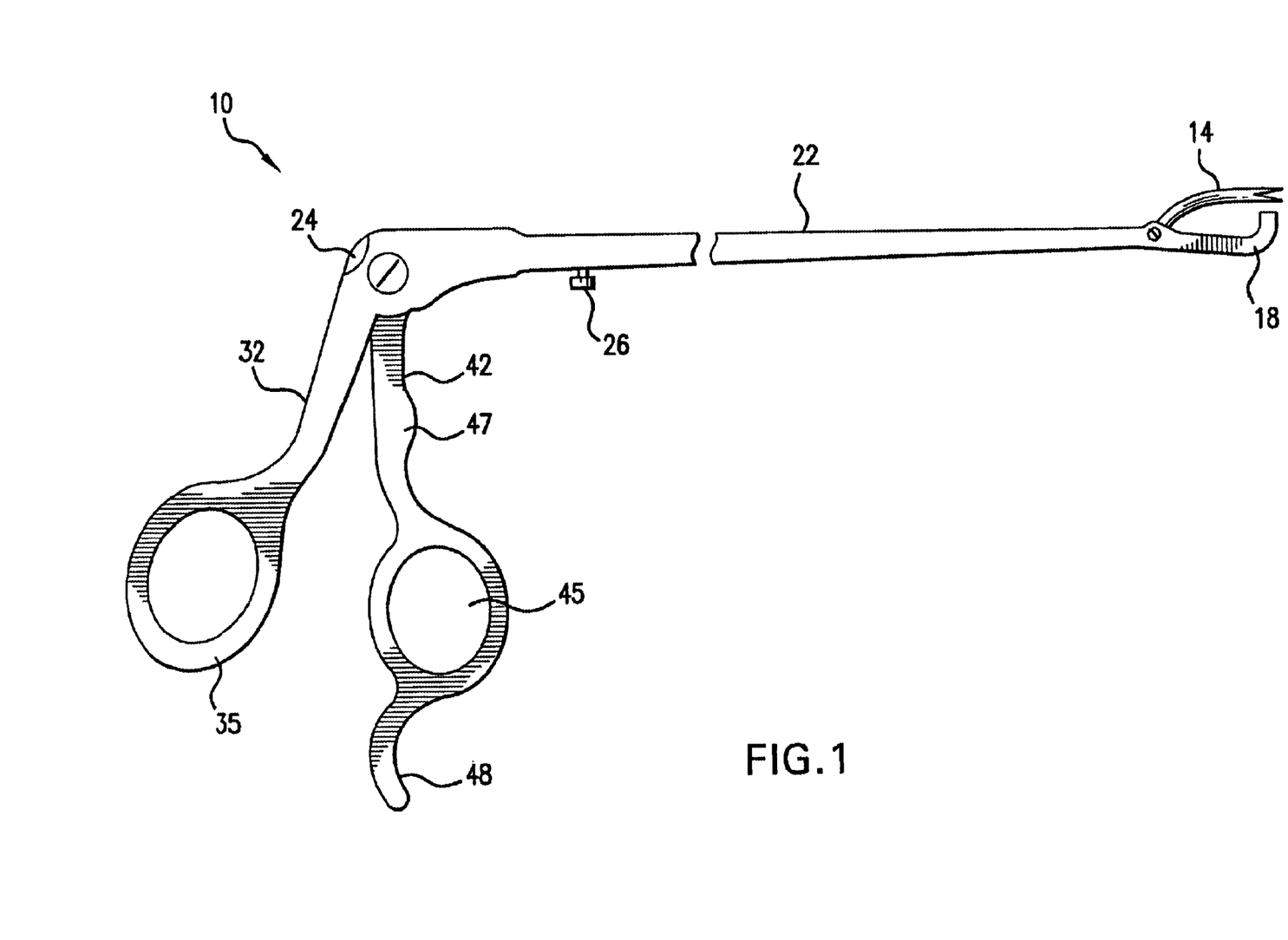
FIG. 1 is a side view of the device.

The structure of the device can be seen with reference to FIG. 1. The suture passer 10 has a pair of opposed jaws. The upper jaw 14 terminates in a guide for a needle. The guide is shown as having a forked end 13. It is possible that another type of guide, such as an eyelet, could be used in its place and without changing the function of the device. The guide aligns with the opening in the lower jaw 18. The lower jaw 18 is formed by a hollow tube having its end turned upwardly so that the opening faces the upper jaw 14. The tube forming the lower jaw 18 connects and is integral with a tube 22 extending from the pair of opposed jaws to a handle.

The handle for the device is formed by a fixed handle 32 and a movable handle 42. The fixed handle 32 has a finger opening 35 at its distal end for the surgeon to grasp. Likewise, the movable handle 42 has a finger opening 45. To increase the comfort in using the device, the movable handle has a contoured surface 47 and a contoured extension 48. The combination of the contoured extension, contoured surface and finger openings in the handle allow the surgeon to easily grasp and manipulate the device.

The movable handle 42 is pivotably connected to the device. Movement of the movable handle toward and away from the fixed handle actuates the upper jaw 14. By manipulating the movable handle, the upper jaw can be moved between an open and closed position. In the closed position, the upper jaw meets with the lower jaw 18.

Figure 2A:
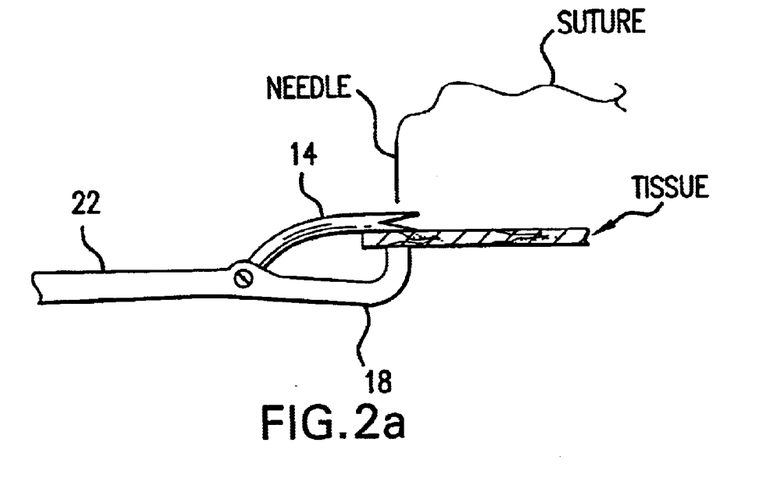
FIGS. 2(a)–2(c) depict the device being used to grasp tissue and pass a suture through the tissue.
Figure 2B:
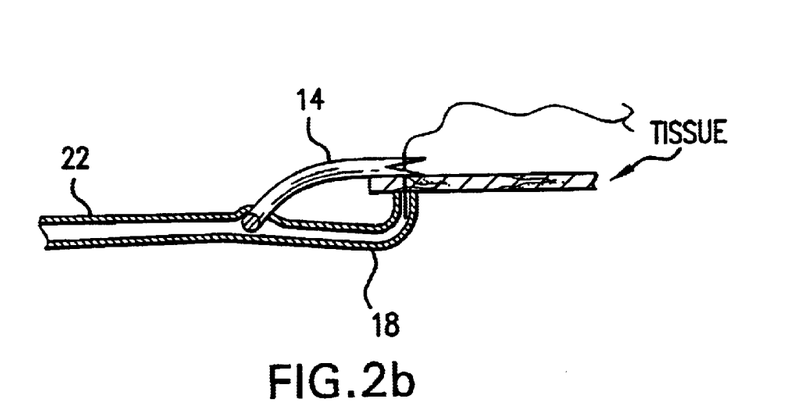
Figure 2C:
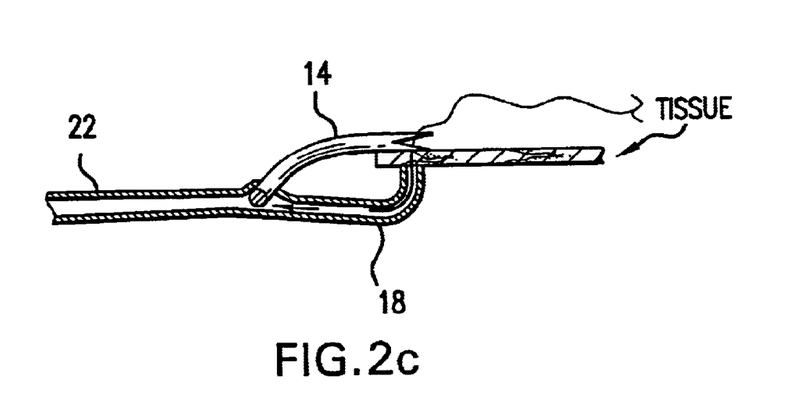

The operation of the device can be seen with reference to FIGS. 2(a)–2(c). Initially, the surgeon manipulates the jaws 14, 18 of the suture passer to grasp the tissue between the opposed jaws. Once the tissue is grasped properly, a suture can be inserted through the tissue. A long flexible needle having a suture attached is passed through the guide of the upper jaw 14. By using the guide of the upper jaw 14, the correct passage of the needle into the lower jaw 18 is ensured.

After the needle passes through the upper jaw 14 and tissue, it enters the opening in the lower jaw 18. The needle is deflected by the lower jaw 18 so that it is bent into the tube 22. The needle is long enough to be deflected preferably out of the back of the suture passer similar to meniscus repair cannulas. The needle is long enough to be grasped and pulled out of a suture passer through opening 24 resulting in a direct passage of the suture or utility loop. The tube can also have a deflector to cause the needle to exit the tube through an opening anywhere along its length. Alternatively, the tube may also have a set screw 26 that can retain the needle in the tube. The surgeon would advance the screw until the needle is retained between the screw and tube inner wall. The needle may also be passed into the tube and remain there until the suture passer is removed from the body. Once the suture passer is removed, the needle can be grasped.

Figure 3:
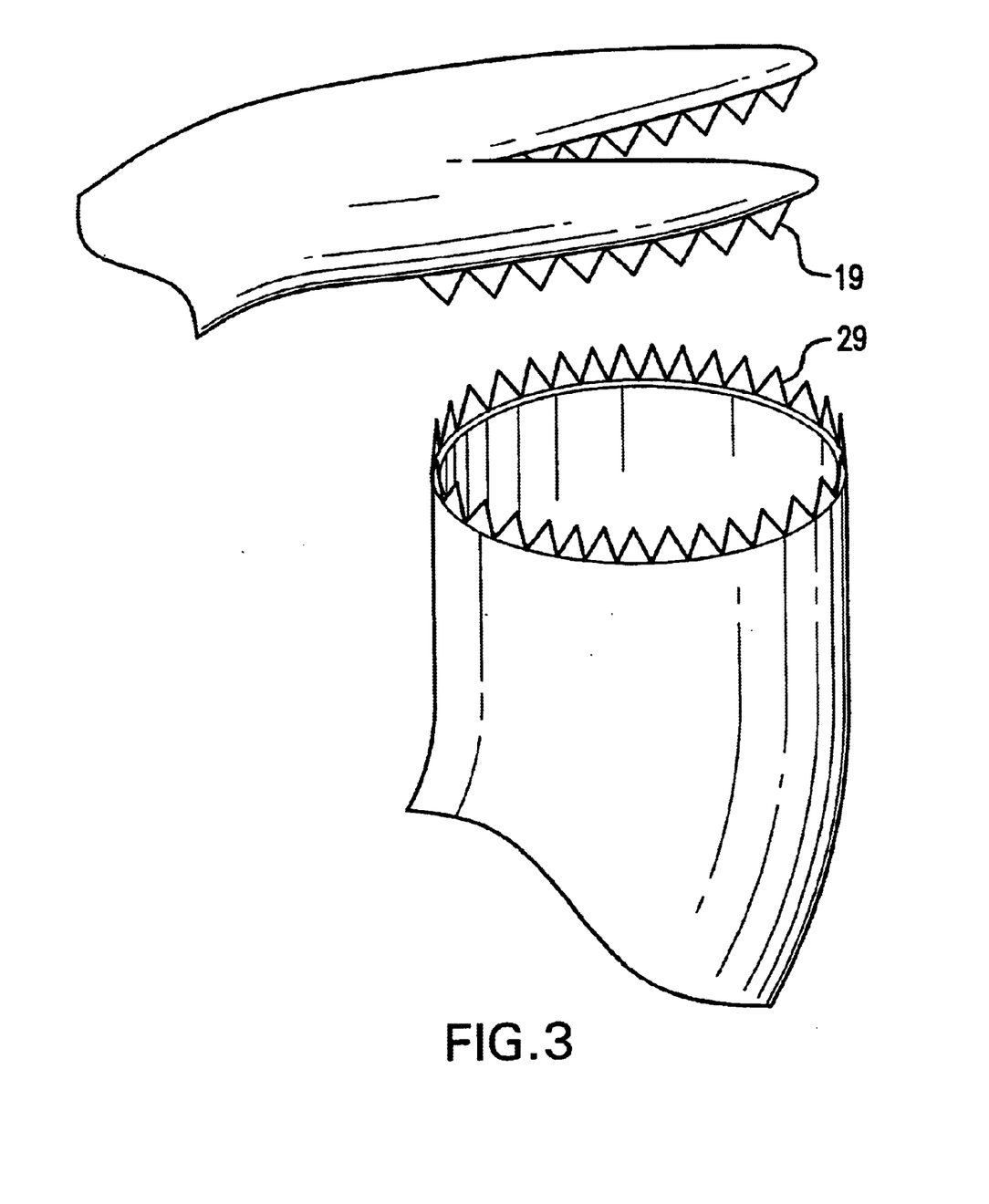
FIG. 3 shows details of the jaws.

Teeth can be provided on the upper and lower jaw. These teeth 19, 29 increase the grip the jaws have on the tissue being manipulated. These teeth can be seen in FIG. 3. While the teeth aid in the grasping and manipulation of the tissue being treated, it causes no harm to the tissue.

Figure 4:
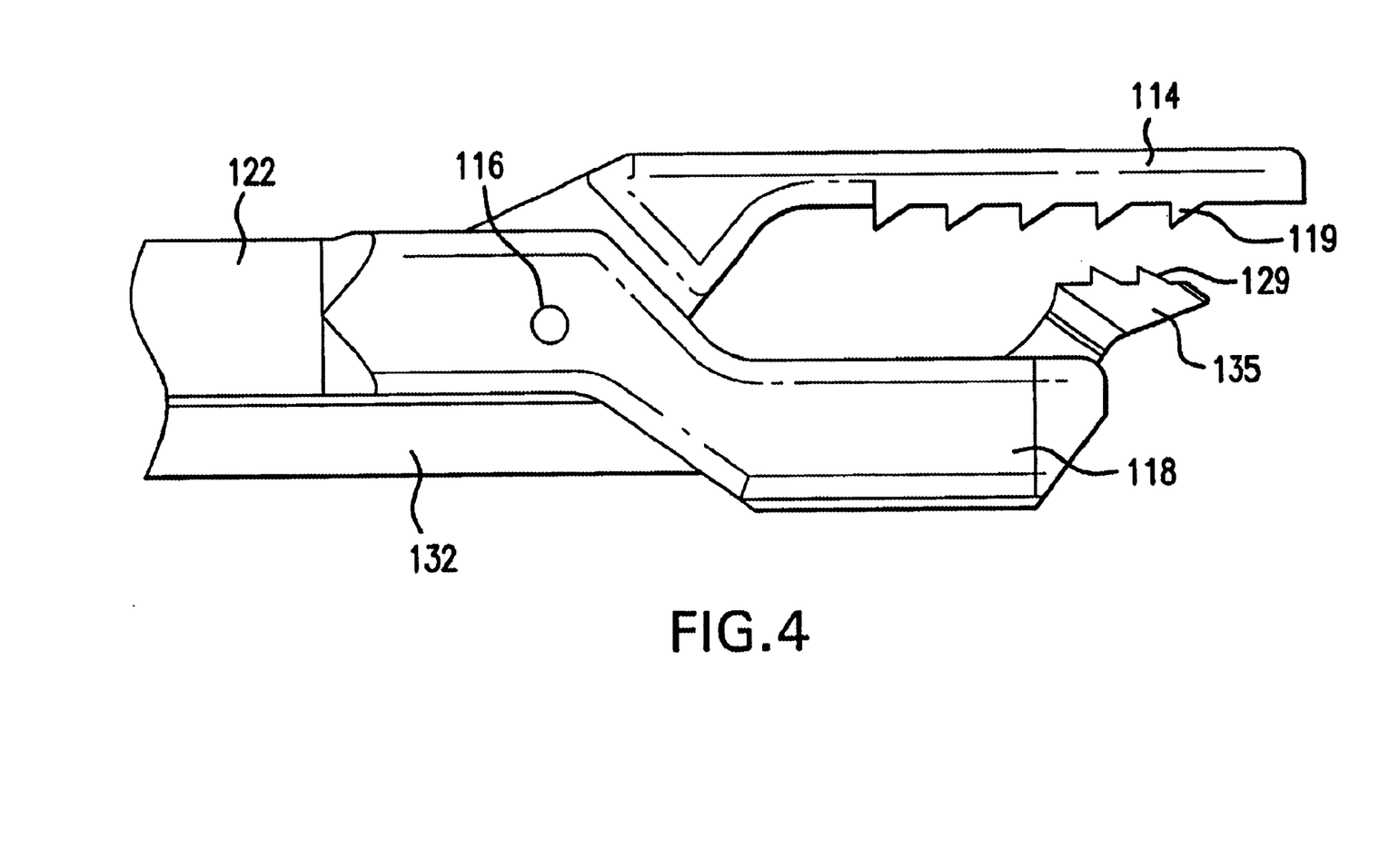
FIG. 4 is a side view of a second embodiment with the jaws closed.

FIG. 4 depicts a second embodiment of the invention. The suture passer has a handle 122, an upper jaw 114 and a lower jaw 118 pivotally connected by a hinge 116. The upper jaw is manipulated by the handle ends, as is well known in the art, and is provided with teeth 119. The suture passes backwards through the suture passer by a passage 132, located below the handle 122. The passage 132 extends through the lower jaw 118. The needle can be grasped at the end of the passage 132. The passage 132 has an enlarged head 135. The enlarged head is provided with teeth 129. The upper teeth 119 and lower teeth 129 serve the same function as was described with reference to the first embodiment. The passage 132, similar to the tube 22 in the first embodiment, can have a set screw for retaining a needle in the passage or an opening along its length and a deflector for causing the needle to exit through the opening. As a third alternative, the needle can remain in the tube as the passer is pulled from the body.

Figure 5:
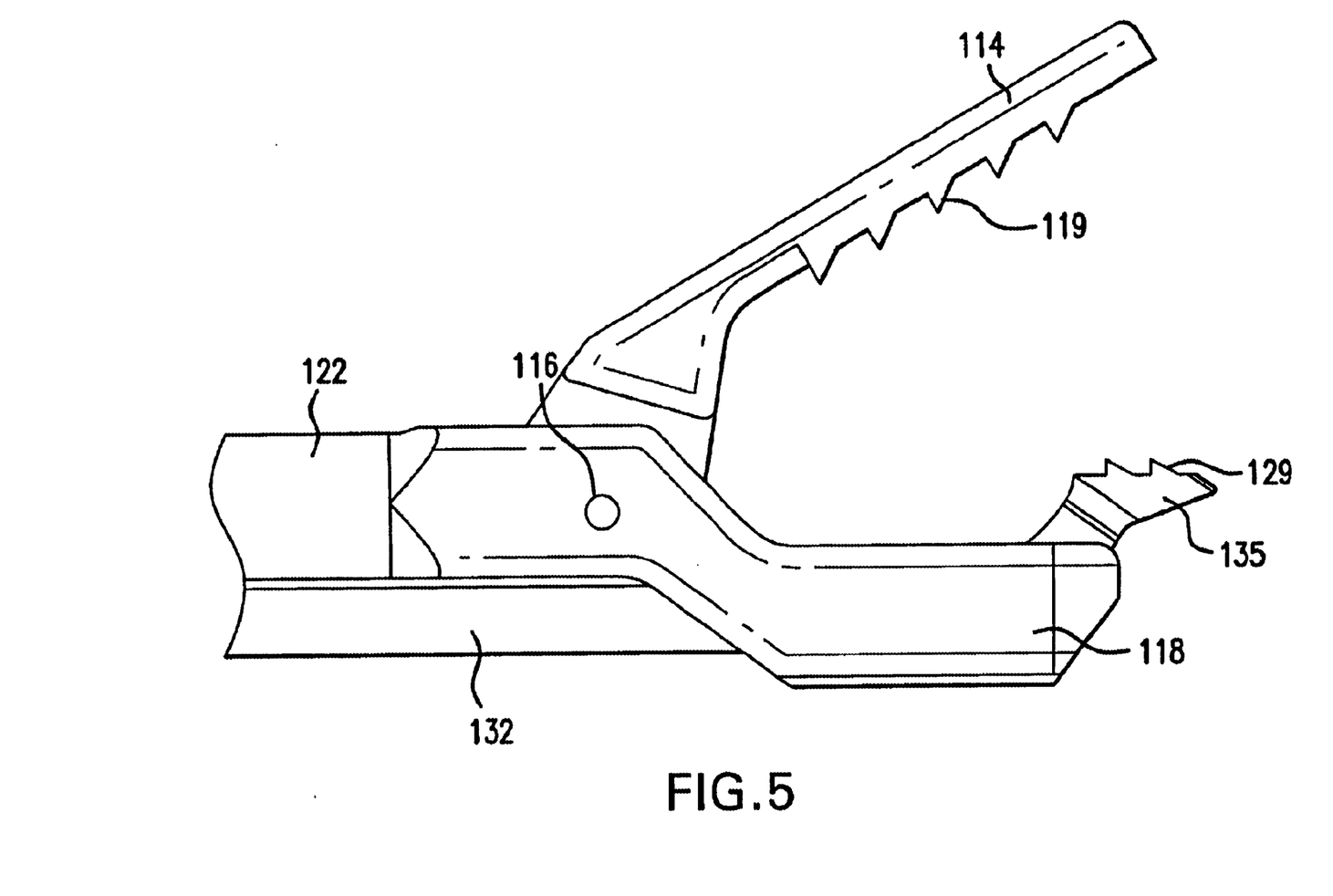
FIG. 5 is a side view of the second embodiment with the jaws open.

FIG. 5 depicts the suture passer with the jaws open as the upper jaw 114 pivots about the hinge 116. This allows the suture passer to grasp the tissue to be sutured.

Figure 6:
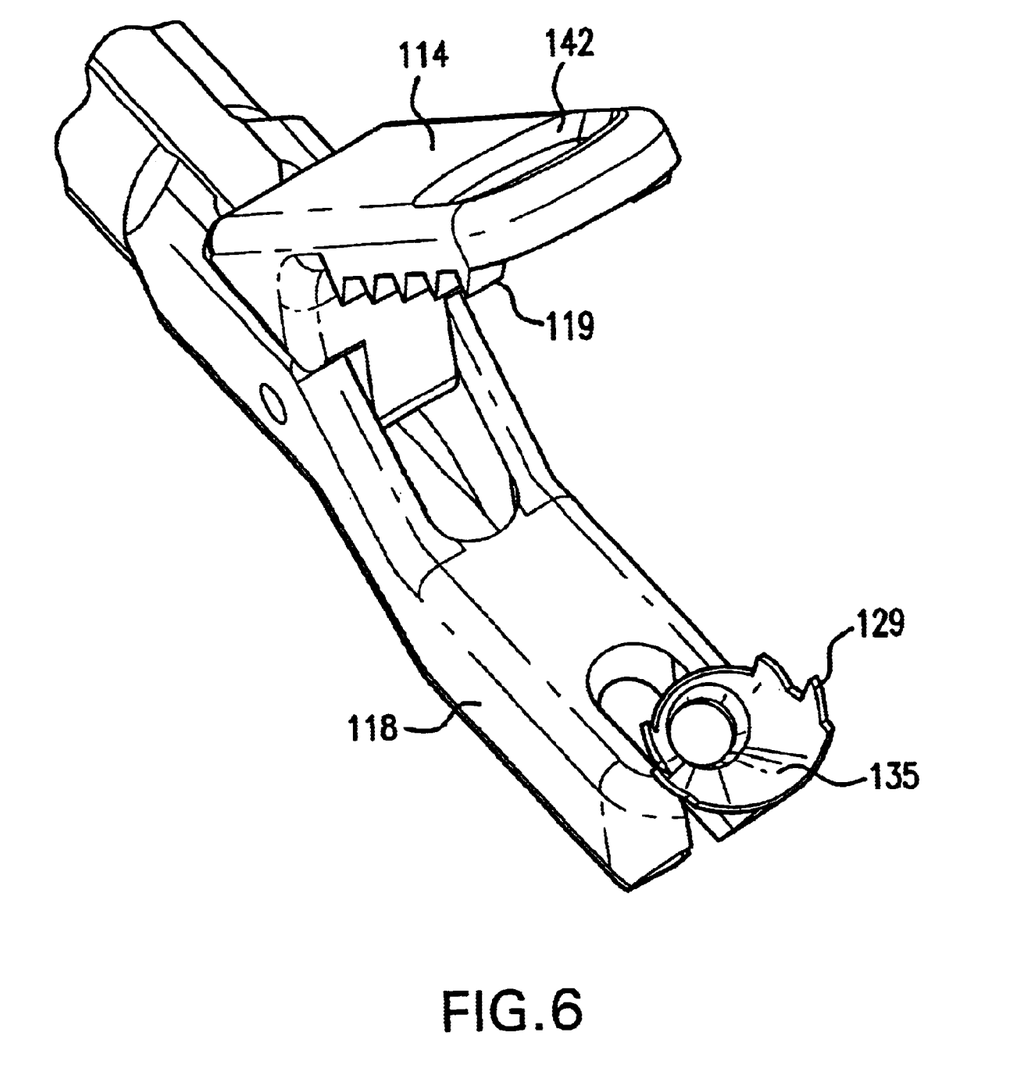
FIG. 6 is a top perspective view of the second embodiment with the jaws open.

FIG. 6 shows a top perspective view of the second embodiment. In this illustration, it can be seen how the enlarged head 135 leads to the passage 132 and how the lower teeth 129 are formed in the upper edge of the enlarged head 135.

Figure 7:
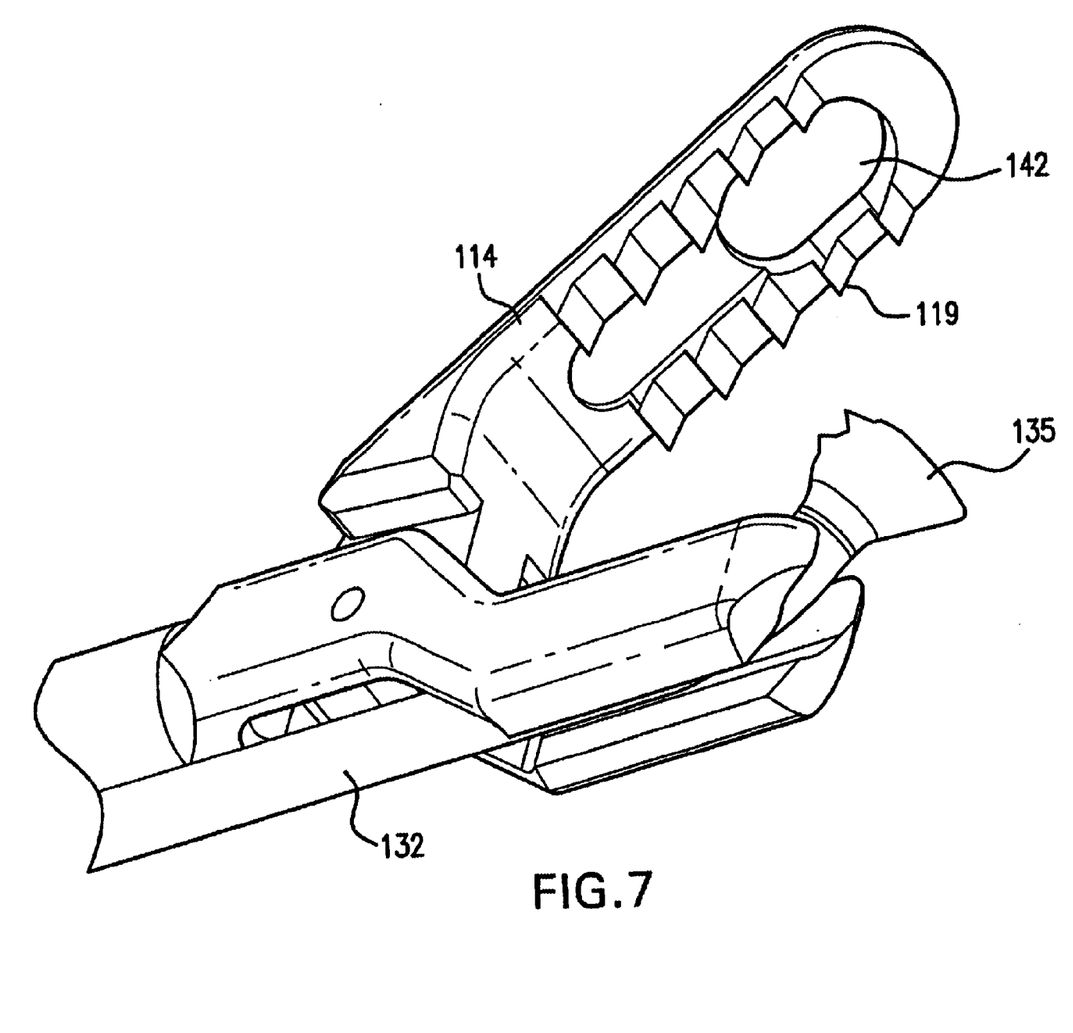
FIG. 7 is a bottom perspective view of the second embodiment with the jaws open.
Figure 8:
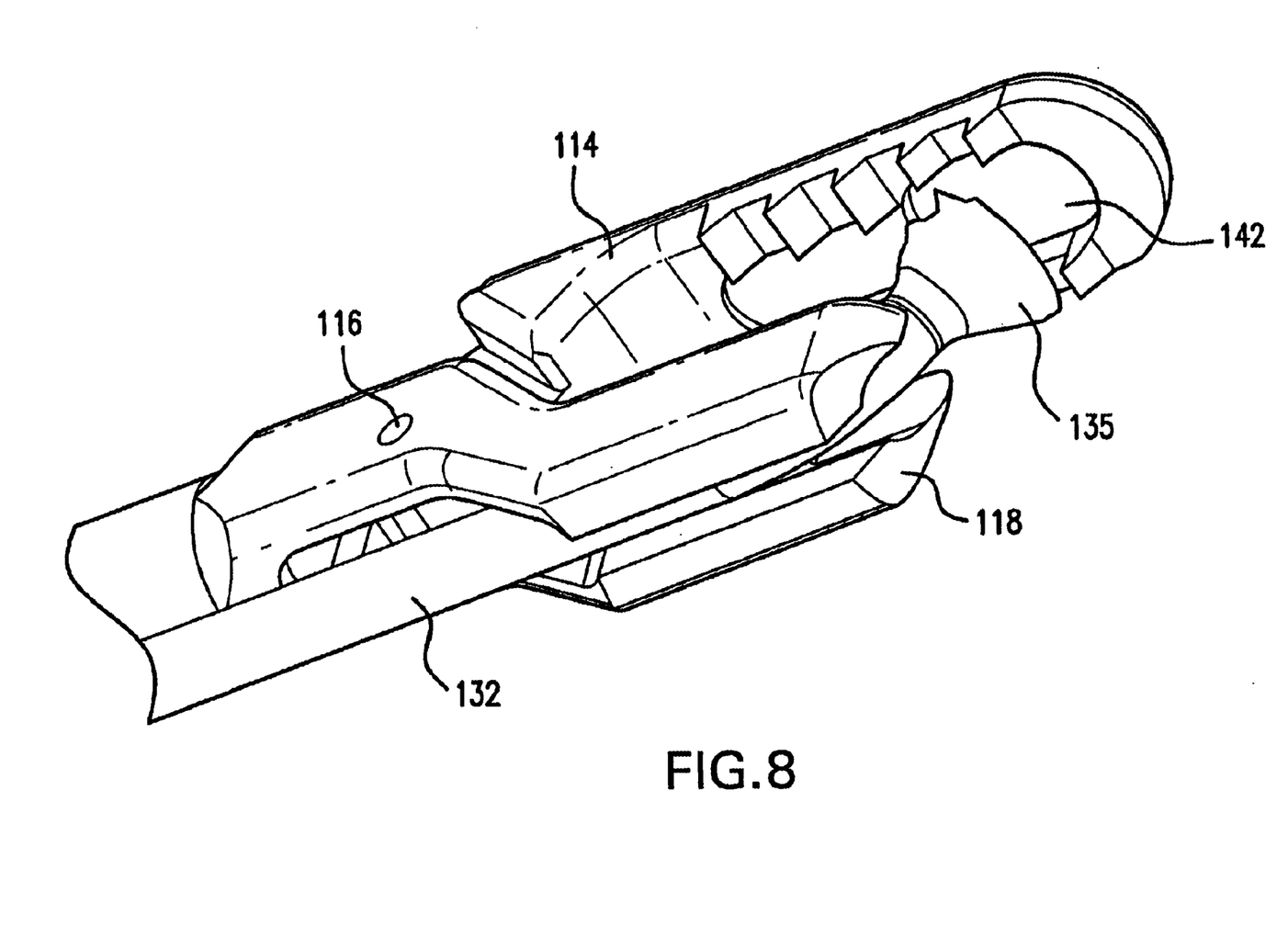
FIG. 8 is a bottom perspective view of the second embodiment with the jaws closed.
Figure 9:
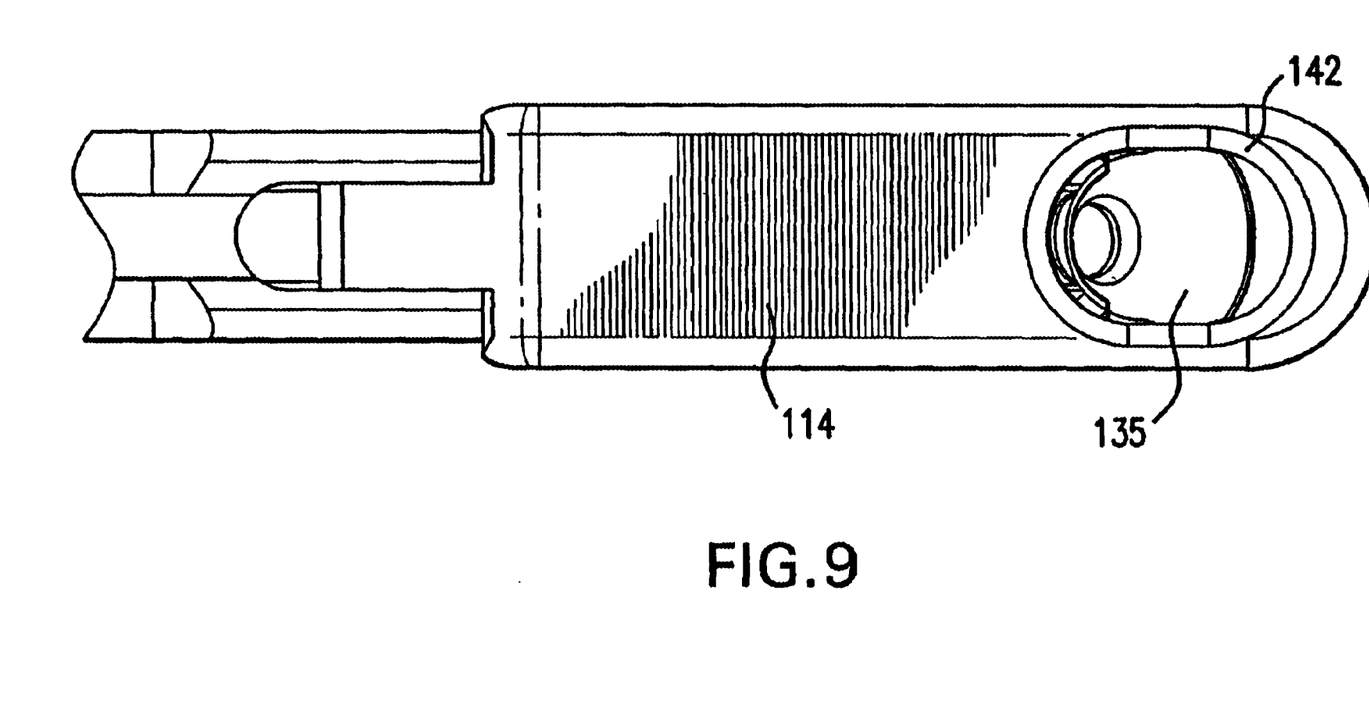
FIG. 9 is a top view of the second embodiment with the jaws closed.

FIG. 7 depicts a bottom perspective view of the suture passer with the jaws open. In this view, the aperture 142 in the upper jaw 114 can be seen. The aperture is shown as being oval, but this is not critical. The bottom perspective view of the jaws closed is seen in FIG. 8. In this view, it is seen how the enlarged head 135 is aligned with the aperture 142 and how the enlarged head angled relative to the passage 132 to guide the suture into the passage. The top view of the jaws in the closed position as seen in FIG. 9. In this view as well, it is seen how the aperture 142 is aligned with the enlarged head 135 and how a suture is passed into the passage 132.

Figure 10:
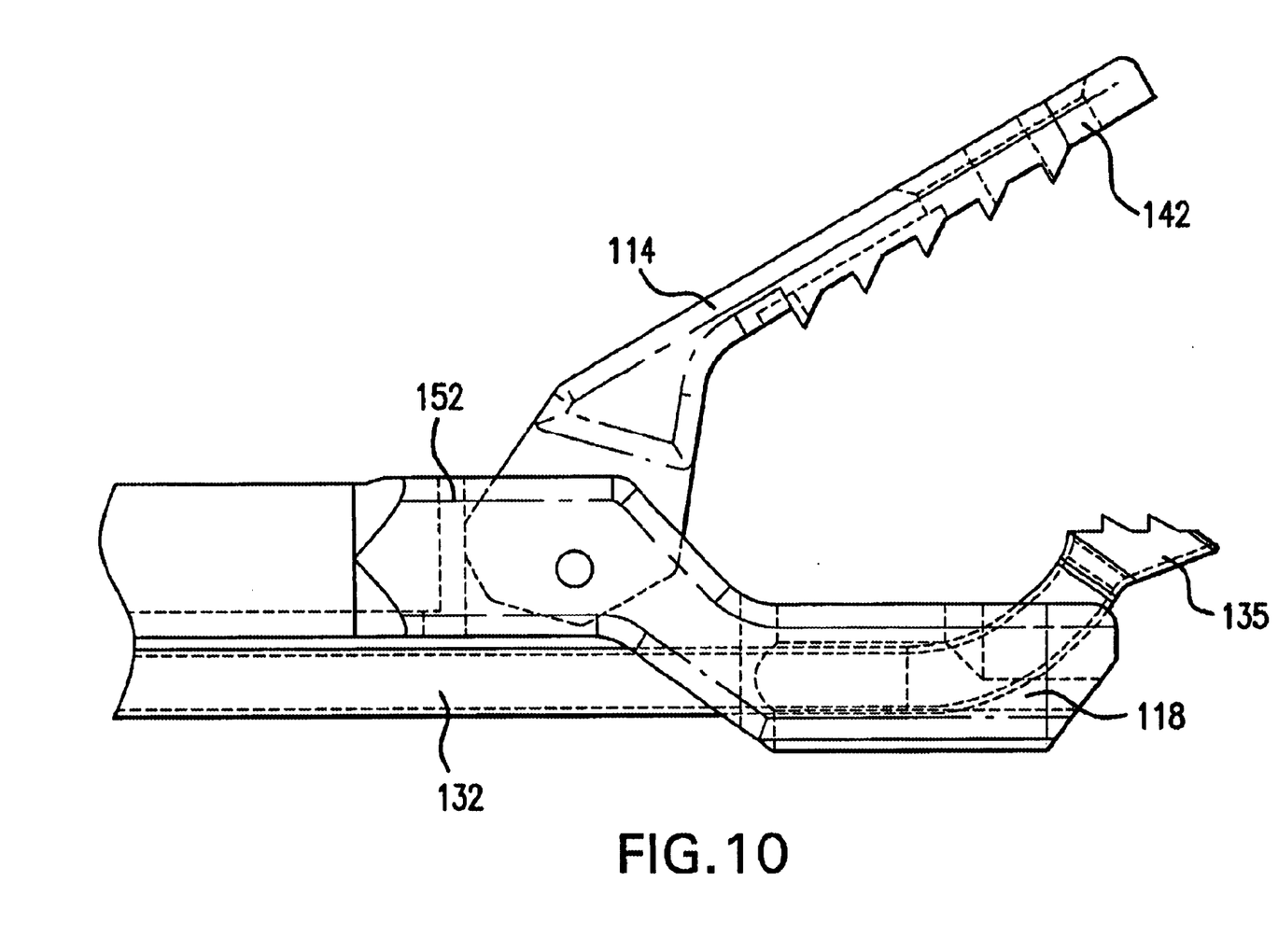
FIG. 10 is a side view of the second embodiment with the jaws open and the internal details shown in phantom.
Figure 11:
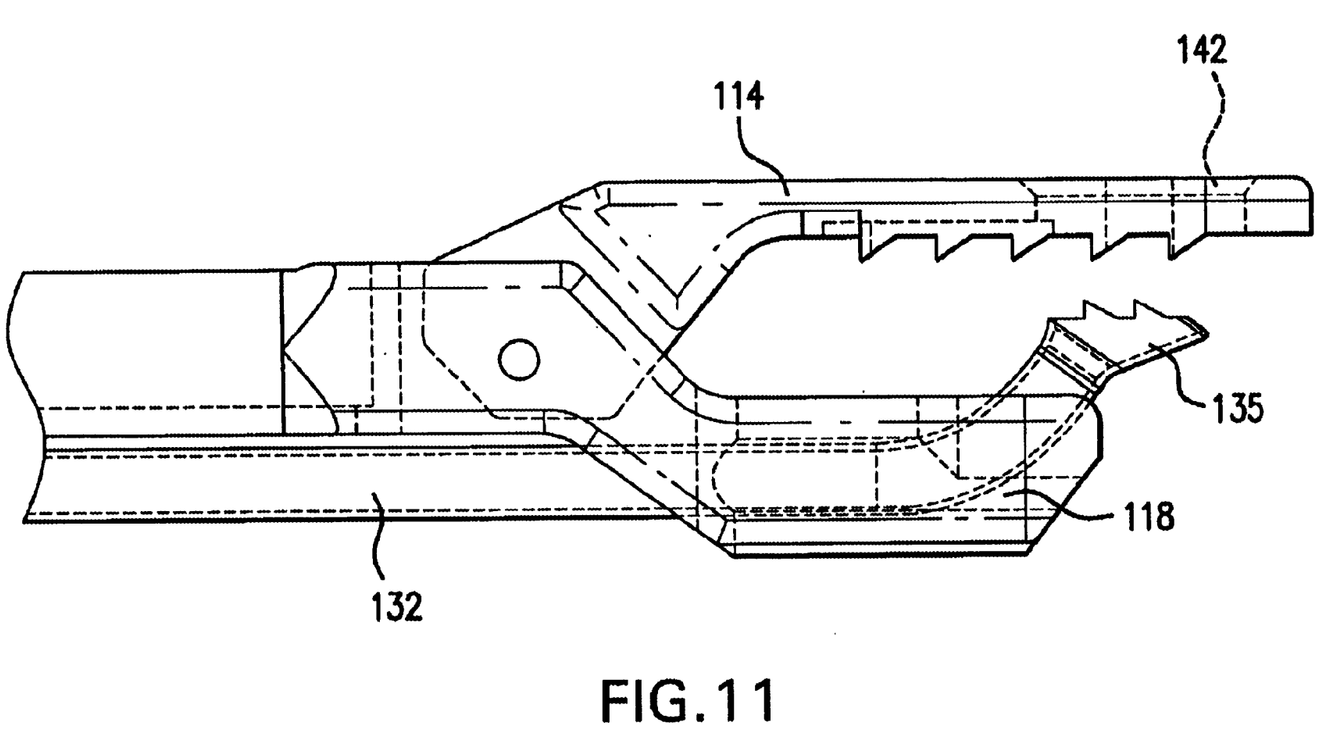
FIG. 11 is a side view of the second embodiment with the jaws closed and the details shown in phantom.

FIGS. 10 and 11 show details of the suture passer with the jaws in both the open and closed positions. In these views, structure that is normally hidden is shown in phantom, including the actuator mechanism 152 housed with the handle 122 for moving the upper jaw 114 relative to the lower jaw 118.

Figure 12A:
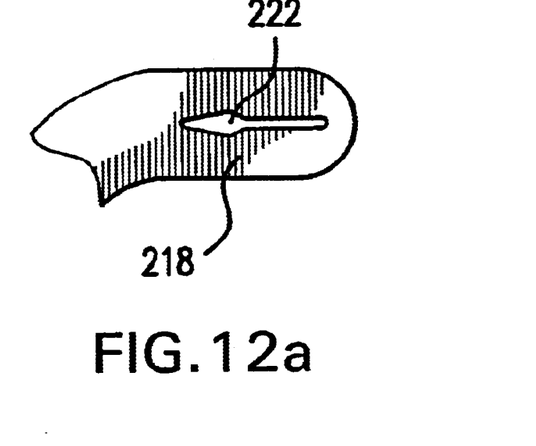
FIGS. 12a and 12b show a third embodiment of the invention with a needle catcher in the lower jaw.
Figure 12B:
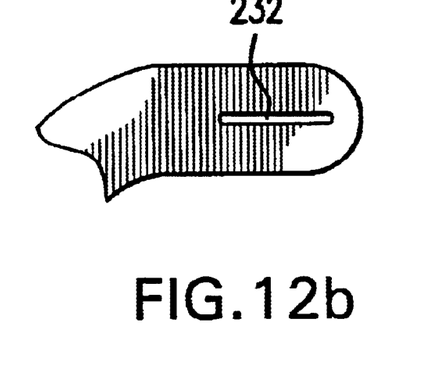

FIGS. 12a and 12b show the lower jaw of the third embodiment. In place of a tube or passage for directing the needle and suture back towards the surgeon, the lower jaw is provided with an aperture sized to resiliently retain the needle. The upper jaw is provided with a forked end or one having an aperture, as seen in the first and second embodiments. The lower jaw is provided with an aperture 222 that is sized and shaped to resiliently retain the needle as it passes through the tissue. Once retained, the surgeon can open the jaws to release the tissue and pull suture passage backwards, carrying the needle and attached suture to the surgeon. In FIG. 12b, an alternative aperture 232 is shown for retaining the needle.

Figure 13A:
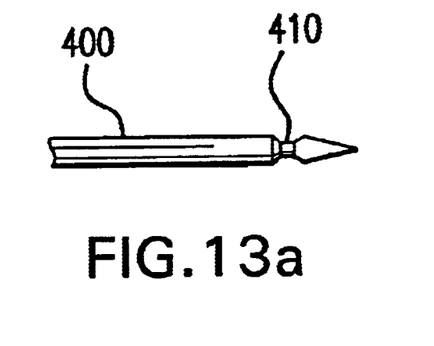
FIGS. 13a and 13b show a needle and attached suture for use with the invention.
Figure 13B:
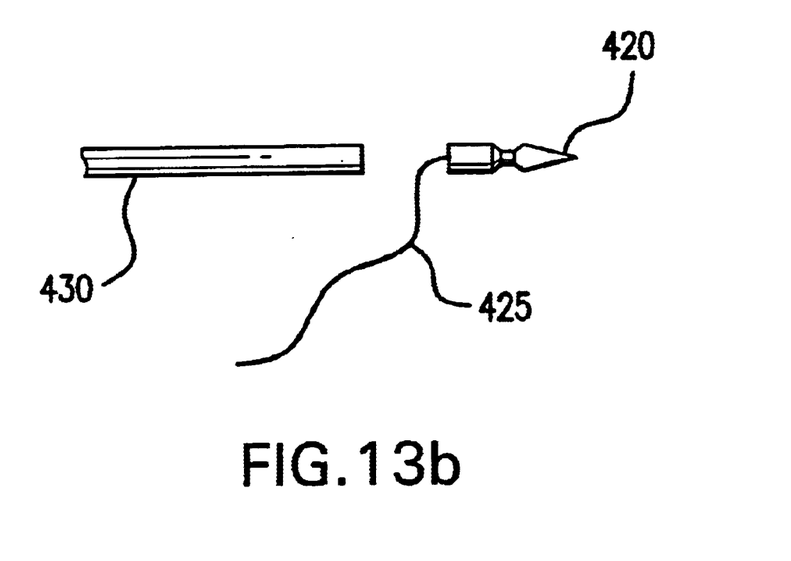

FIG. 13a shows a needle useable with the third embodiment. The needle 400 is provided with an indentation 410 for resiliently lodging within an aperture in the lower jaw. In FIG. 13b, a short needle 420 having a suture 425 attached is used with a pusher 430 for use by the surgeon in passing the needle through the suture passer and tissue.

By using the device, a surgeon is ensured of the quick and accurate passage of sutures through tissue. The device allows for the easy manipulation of tissue and the correct placement of a suture. The efficient manner and easy handling of the suture passer allows a reduction in fatigue of a surgeon during the operation.

What is claimed is:

1. A suture passer, comprising:
   a handle,
   an upper jaw and lower jaw extending from said handle, said upper jaw and lower jaw movable relative to one another for grasping tissue,
   a suture guide formed in said upper jaw, and
   a suture returner formed in said lower jaw for allowing a surgeon to easily grasp a suture after it has passed through tissue, said suture returner comprising a passage in said lower jaw in communication with a passage in said handle further comprising a set screw in said handle for retaining a needle in said passage.

2. The suture passer of claim 1, wherein said suture guide is a forked end.

3. The suture passer of claim 1, wherein said suture guide is an aperture in said upper jaw.

4. The suture passer of claim 1, wherein said suture returner comprises an aperture in said lower jaw, said aperture sized to retain a needle attached to said suture.

5. A suture passer, comprising:
   a handle,
   an upper jaw and lower jaw extending from said handle, said upper jaw and lower jaw movable relative to one another for grasping tissue,
   a suture guide formed in said upper jaw, and
   a suture returner formed in said lower jaw for allowing a surgeon to easily grasp a suture after it has passed through tissue, wherein said suture returner comprises a passage below said handle, said passage terminating at said lower jaw.

6. The suture passer of claim 5, wherein said passage terminates in an enlarged head.

7. The suture passer of claim 6, where in said enlarged head has teeth.

8. The suture passer of claim 5, wherein said passage terminates in alignment with said suture guide.

9. A suture passer, comprising:

a handle, an upper jaw and lower jaw extending from said handle, said upper jaw and lower jaw movable relative to one another for grasping tissue, a suture guide formed in said upper jaw, and a suture returner formed in said lower jaw for allowing a surgeon to easily grasp a suture after it has passed through tissue, further comprising teeth on said upper jaw.

10. A method for suturing tissue, comprising:

grasping tissue between an upper jaw and lower jaw of a suture passer, passing the needle and suture through a suture guide in the upper jaw, passing the needle and suture through the tissue, and passing the needle and suture into a suture returner, wherein passing the needle and suture into the suture returner comprises passing the needle and suture into a passage below a handle of the suture passer.

11. The method of claim 10, wherein passing the needle and suture through the suture guide comprises passing the needle and suture between forked ends of the upper jaw.

12. The method of claim 10, wherein passing the needle and suture through the suture guide comprises passing the needle and suture through an aperture in the upper jaw.

13. The method of claim 10, wherein passing the needle and suture into the suture returner comprises passing the needle and suture into a passage into a slot in the jaw sized to retain the needle.

14. The method of claim 10, wherein the jaws open and the needle remains in the lower jaw as the suture passer is withdrawn.

15. A method for suturing tissue, comprising:

grasping tissue between an upper jaw and lower jaw of a suture passer, passing the needle and suture through a suture guide in the upper jaw, passing the needle and suture through the tissue, and passing the needle and suture into a suture returner, wherein passing the needle and suture into the suture returner comprises passing the needle and suture into a passage in the lower jaw and suture passer handle.

16. In combination, a suture passer and needle, comprising a suture passer comprising a upper and lower jaw for grasping tissue, and a handle for manipulating said suture passer, said lower jaw having an aperture, said needle comprising a shaft, a sharpened end at one end of the shaft, a notch in diametrically opposed sides of said shaft spaced from said sharpened end, wherein said sharpened end enters said aperture in said lower jaw and said notch retains the needle in said aperture.

17. The needle of claim 16, further comprising a pusher for pushing said needle through tissue.

* * * * *